United States Patent

Litkowski et al.

[11] Patent Number: 6,086,374
[45] Date of Patent: *Jul. 11, 2000

[54] METHODS OF TREATMENT USING BIOACTIVE GLASS

[75] Inventors: Leonard J. Litkowski, Baltimore; Gary D. Hack, Columbia, both of Md.; David C. Greenspan, Gainesville, Fla.

[73] Assignee: USBiomaterials Corp., Alachua, Fla.

[ * ] Notice: This patent issued on a continued prosecution application filed under 37 CFR 1.53(d), and is subject to the twenty year patent term provisions of 35 U.S.C. 154(a)(2).

[21] Appl. No.: 08/789,909

[22] Filed: Jan. 29, 1997

Related U.S. Application Data

[63] Continuation-in-part of application No. 08/597,936, Feb. 7, 1996, abandoned.
[60] Provisional application No. 60/010,795, Jan. 29, 1996.

[51] Int. Cl.$^7$ ...................................................... A61C 5/00
[52] U.S. Cl. ..................................... 433/217.1; 433/228.1
[58] Field of Search .............................. 433/228.1, 227.1, 433/216, 215, 217.1; 106/35; 424/49, 52

[56] References Cited

U.S. PATENT DOCUMENTS

| | | | |
|---|---|---|---|
| Re. 36,035 | 1/1999 | Usen et al. | 222/1 |
| 3,981,736 | 9/1976 | Broemer et al. | 501/10 |
| 4,057,621 | 11/1977 | Pashley et al. | 424/49 |
| 4,239,113 | 12/1980 | Gross et al. | 206/568 |
| 4,538,990 | 9/1985 | Pashley | 433/217.1 |
| 4,605,415 | 8/1986 | Richez | 623/16 |
| 4,775,592 | 10/1988 | Akahane et al. | 428/406 |
| 4,775,646 | 10/1988 | Hench et al. | 501/2 |
| 4,783,429 | 11/1988 | Shibuya et al. | 501/5 |
| 4,851,046 | 7/1989 | Low et al. | 106/35 |
| 4,920,082 | 4/1990 | Danielson | 501/59 |
| 5,037,639 | 8/1991 | Tung | 424/57 |
| 5,120,340 | 6/1992 | Duncheyne et al. | 65/17.5 |
| 5,204,106 | 4/1993 | Schepers et al. | 424/423 |
| 5,236,458 | 8/1993 | Ducheyne et al. | 623/16 |
| 5,268,167 | 12/1993 | Tung | 424/52 |
| 5,296,026 | 3/1994 | Monroe et al. | 106/35 |
| 5,314,474 | 5/1994 | Helms et al. | 623/16 |
| 5,340,776 | 8/1994 | Paschke et al. | 501/11 |
| 5,356,951 | 10/1994 | Yearn et al. | 523/116 |
| 5,425,771 | 6/1995 | Helms et al. | 623/16 |
| 5,427,768 | 6/1995 | Tung | 424/52 |
| 5,429,996 | 7/1995 | Kaneko | 501/35 |
| 5,432,130 | 7/1995 | Rheinberger et al. | 501/32 |
| 5,571,502 | 11/1996 | Winston et al. | 424/52 |
| 5,603,922 | 2/1997 | Winston et al. | 424/49 |
| 5,605,675 | 2/1997 | Usen et al. | 424/49 |
| 5,614,175 | 3/1997 | Winston et al. | 424/52 |
| 5,628,429 | 5/1997 | Usen et al. | 222/1 |
| 5,641,347 | 6/1997 | Grabowski | 433/228.1 |
| 5,645,853 | 7/1997 | Winston et al. | 424/440 |

(List continued on next page.)

FOREIGN PATENT DOCUMENTS

| | | |
|---|---|---|
| WO96/10985 | 10/1995 | WIPO . |
| WO96/00536 | 11/1996 | WIPO . |
| WO97/27148 | 7/1997 | WIPO . |
| WO13852 | 3/1999 | WIPO . |

OTHER PUBLICATIONS

Hench, Larry L. and West, Jon K., "Biological Applications of Bioactive Glasses," *Life Chemistry Reports*, v. 13, p. 187–241. (1996).

*Primary Examiner*—John J. Wilson
*Attorney, Agent, or Firm*—Burns, Doane, Swecker & Mathis, L.L.P.

[57] ABSTRACT

A novel silica based bioactive glass composition that can be used in conjunction with a delivery agent such as a toothpaste, gel, etc. having a particle size range <90 $\mu$gm which will form a rapid and continuous reaction with body fluids due to the immediate and long term ionic release of Ca and P from the core silica particles, to produce a stable crystalline hydroxy carbonate apatite layer deposited onto and into the dentin tubules for the immediate and long term reduction of dentin hypersensitivity and tooth surface remineralization.

22 Claims, 12 Drawing Sheets

U.S. PATENT DOCUMENTS

| | | | |
|---|---|---|---|
| 5,735,942 | 4/1998 | Litkowski et al. | 106/35 |
| 5,741,479 | 4/1998 | Masterman et al. | 424/49 |
| 5,766,328 | 6/1998 | Nakabayashi et al. | 106/35 |
| 5,817,296 | 10/1998 | Winston et al. | 424/49 |
| 5,833,957 | 11/1998 | Winston et al. | 424/49 |
| 5,858,333 | 1/1999 | Winston et al. | 424/57 |
| 5,860,565 | 1/1999 | Winston et al. | 222/1 |
| 5,866,102 | 2/1999 | Winston et al. | 424/52 |
| 5,895,641 | 4/1999 | Usen et al. | 424/52 |

METHODS OF TREATMENT USING BIOACTIVE GLASS

This application is a continuation-in-part application of U.S. application Ser. No. 08/597,936 filed Feb. 7, 1996, now abandoned, the disclosure of which is hereby incorporated by reference. This application further claims the benefit of copending U.S. Provisional Application Ser. No. 60/010,795 filed Jan. 29, 1996, the disclosure of which is hereby incorporated by reference.

FIELD OF THE INVENTION

The present invention relates to bioactive glass compositions. More particularly, the present invention relates to improved compositions of bioactive glass including particles having combinations of size ranges significantly lower than previous compositions. The present invention also relates to various methods of treatment including the use of such bioactive glass compositions.

BACKGROUND OF THE INVENTION

Human tooth enamel naturally undergoes a process of demineralization. Exposure of enamel to saliva and food slowly leaches minerals from teeth and eventually leads to increased susceptibility to decay. This process of demineralization results in incipient caries which are typically very small defects in the enamel surface that are thus far usually left untreated. Carious dentin demineralization also may occur in patients that have exposed regions of dentin resulting from decay below the cementum-enamel junction. Accordingly, there has been much work associated with slowing this natural process of demineralization including the application of fluoride and other topical treatments.

For example, U.S. Pat. No. 5,427,768 discloses calcium phosphate solutions which are supersaturated with respect to calcium phosphate solids and carbon dioxide. The solutions deposit calcium phosphate compounds with or without fluoride on and in the tooth weaknesses such as dental caries, exposed root, or dentin. U.S. Pat. Nos. 5,268,167 and 5,037,639 disclose the use of amorphous calcium compounds such as amorphous calcium phosphate, amorphous calcium phosphate fluoride and amorphous calcium carbonate phosphate for use in remineralizing teeth. These amorphous compounds, when applied to dental tissue prevent and/or repair dental weaknesses. The disadvantages of these methods include (1) a low pH necessary for the application which can be an irritant, (2) rapid reaction results in a very short term effect, (3) since these methods use solutions, the actual reactions are difficult to control from patient to patient, and (4) since the reactions are rapid and of short duration, the procedure must be repeated to maintain the effect. Also, both methods require maintaining at least one solution with pressurized $CO_2$ prior to mixing delivery which makes the method difficult to incorporate into an over-the-counter procedure.

Demineralization eventually leads to cavitation of enamel coating such that there is exposure of the underlying tooth structure. Typically, this type of decay is treated by drilling out the decayed region and inserting a semi-permanent filling material. However, there is a need for a less invasive means of arresting and reversing decay.

Prophylactic pit and fissure sealants have become widely used in preventing decay in areas that are particularly at risk for decay. These sealants have included polymer or other cements that require a dry application and the use of a fixing agent. These sealants are temporary and do not provide for an optimal seal.

Liners and bases are materials that are used to treat newly exposed tooth surfaces such as those surfaces exposed by drilling. After a cavity is prepared, it is common practice to apply a liner or base before filling the cavity with a filling material. A liner is a thin coating of material and a base is a thicker coating. Liner and base materials are designed to decrease permeability of dentin at the tooth material interface and protect against microleakage around and through the fill material and to seal dentin tubules. Earlier liners or "cavity varnishes" include materials such as organic "gums" dissolved in organic solvents. Upon evaporation of the organic solvent, the gum is left behind. Disadvantages associated with these organic gums are well documented and include leaky junctions, lack of adherence, acid vulnerability, etc. Another method of lining is disclosed in U.S. Pat. No. 4,538,990 which describes applying a 1 to 30% w/v neutral oxalate salt solution, such as dipotassium oxalate to the smear layer and then applying a 0.5 to 3% w/v of an acidic oxalate salt solution such as monopotassium monohydrogen oxalate to the layer. Research has shown poor seal occlusion of the tubules with this method.

U.S. Pat. No. 5,296,026 discloses glass phosphate cement compositions and methods for their use as surgical implant materials to fill cavities in bone and canals in teeth. The cement compositions include $P_2O_5$, CaO, SrO and $Na_2O$ in combination with an aqueous liquid with or without therapeutic agents. Mixing the powder and liquid results in a hardening reactions. When the cement is implanted into hard tissue, it serves as a filler/graft material and along with the release of leachable constituents it can assist in the healing and maintenance of healthy bone.

Various bioactive and biocompatible glasses have been developed as bone replacement materials. Studies have shown that these glasses will induce or aid osteogenesis in a physiologic systems. Hench et al, *J. Biomed. Mater. Res.* 5:117–141 (1971). The bond developed between the bone and the glass has been demonstrated to be extremely strong and stable. Piotrowski et al., *J. Biomed. Mater. Res.* 9:47–61 (1975). Toxicology evaluation of the glasses has shown no toxic effects in bone or soft tissue in numerous in vitro and in vivo models. Wilson et al., *J. Biomed. Mater. Res.* 805–817 (1981). The glass has been reported to be bacteriostatic or bacteriocidal most likely related to the change in pH induced by the dissolution of the ions from the surface of the glass and lack of bacterial adherence to the glass surface. Stoor et al, Bioceramics Vol. 8 p. 253–258 Wilson et al (1995).

The bonding of the glass to bone begins with the exposure of the glass to aqueous solutions. $Na^+$ in the glass exchanges with H+ from the body fluids causing the pH to increase. Ca and P migrate from the glass forming a Ca—P rich surface layer. Underlying this Ca—P rich is a layer which becomes increasingly silica rich due to the loss of Na, Ca and P ions (U.S. Pat. No. 4,851,046).

The behavior of the bioactive glass as solid implants in a dental application was reported by Stanley et al., Journal of Prostetic Dentistry, Vol. 58, pp. 607–613 (1987). Replicate tooth forms were fabricated and implanted into extracted incisor sockets of adult baboons. Successful attachment of the implants to surrounding bone was seen after histologic examination at six months. Clinical application of this technique is presently available for human use. Endosseous Ridge Maintenance Implant ERMI®. Particulate bioactive glass has been used for periodontal osseous defect repair (U.S. Pat. No. 4,851,046) utilizing a size range of 90–710 $\mu$m and a compositional range described in the following chart.

| Component | Weight Percentage |
| --- | --- |
| $SiO_2$ | 40–55 |
| CaO | 10–30 |
| $Na_2O$ | 10–35 |
| $P_2O_5$ | 2–8 |
| $CaF_2$ | 0–25 |
| $B_2O_3$ | 0–10 |

Previously described data has shown that 60% silica is beyond the limit of bioactive melt derived glasses. Okasuki et al. Nippon Seramikbusu Kyokai Gakijutsu Konbuski, Vol. 99, pp. 1–6 (1991).

The 90–710 μm size range was determined to be the most effective for periodontal applications when in direct contact with bone. However, size ranges smaller than 90 μm were ineffective due to their high rate of reactivity and rapid resorption at the bony site. Moreover, size ranges smaller than 90 μm were determined to be ineffective in soft tissue sites also due to the presumption that the smaller particles were removed by macrophages (see U.S. Pat. No. 4,851, 046). A size range of less than 200 μm was also found to be ineffective in certain bone defects (see U.S. Pat. No. 5,204, 106) due to the high rate of reactivity.

U.S. Pat. No. 4,239,113 ("the '113 patent") also describes the use of a bone cement. The '113 patent only discloses bioactive glass ceramic powder having a particle size of 10–200 microns. Moreover, the '113 patent also requires the use of methylmethacrylate (co)polymers and vitreous mineral fibers.

None of the foregoing methods or compositions provide for the combined advantages of both easy application and adherence to tooth structure including penetration into very small tooth structure defects and the opportunity for continued chemical and physical interaction with tooth structure after application.

Accordingly, it is an object of the present invention to provide a composition capable of chemical and physical interaction with tooth structure that is easily applied and readily adherent to tooth structure.

It is a further object of the invention to provide a method of using such a bioactive glass composition to treat a variety of dental and other conditions.

SUMMARY OF THE INVENTION

The present invention relates to, for example, a bioactive glass composition including particulate bioactive and biocompatible glass including by weight percentage:

| | |
| --- | --- |
| $SiO_2$ | 40–60 |
| CaO | 10–30 |
| $Na_2O$ | 10–35 |
| $P_2O_5$ | 2–8 |
| $CaF_2$ | 0–25 |
| $B_2O_3$ | 0–10 |
| $K_2O$ | 0–8 |
| MgO | 0–5, | the particulate bioactive and biocompatible glass including particles less than 90 μm and an effective remineralizing amount of particles less than about 10 μm. The present invention also relates to various methods of dental treatment including remineralization, sealing fissures and/or pits, lining tooth structure, treating decay, capping pulp, treating sensitive post surgical tooth structure, sealing dentinal tubules, and surface for tissue regeneration.

DETAILED DESCRIPTION OF THE INVENTION

Figure 1:
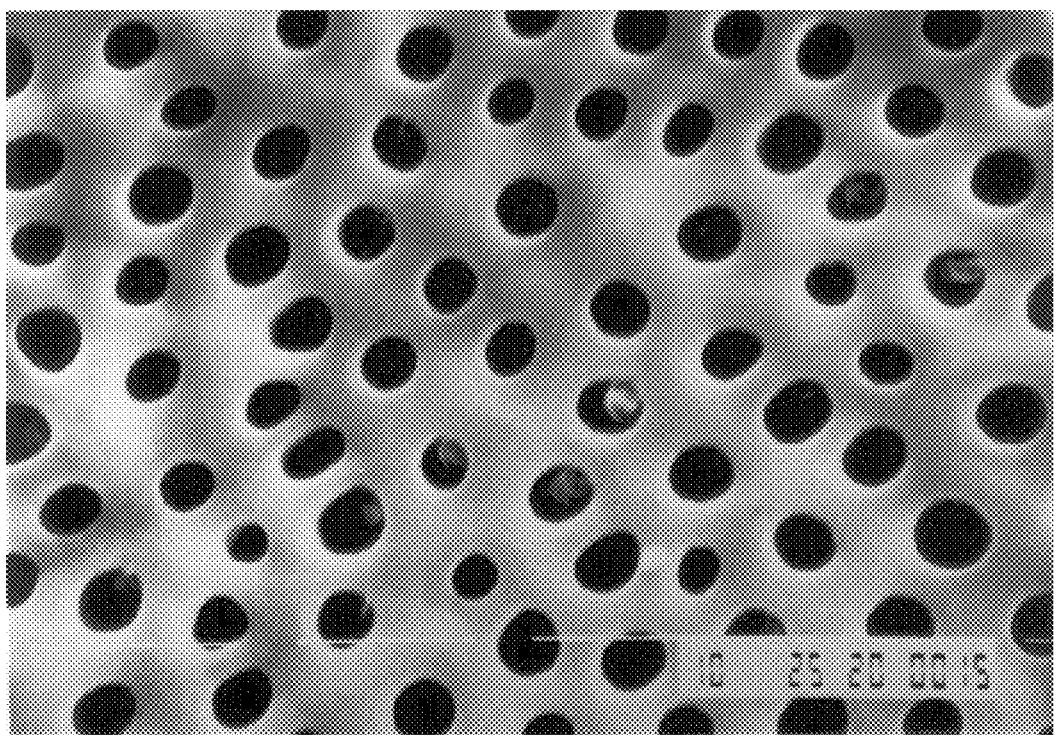
FIG. 1 is a dentin control surface that has been treated with 37% phosphoric acid for 30 seconds to remove any smear layer after sectioning and grinding to emulate clinical sensitivity. The surface has not been treated with bioactive glass in accordance with the present invention (2000× magnification).

The present invention provides a bioactive glass composition which is useful in, for example, enamel remineralization, incipient caries remineralization, carious dentin remineralization, caries prevention, arresting decay, reversing decay, anti-caries, pit and fissure sealants, prophylactic pastes, fluoride treatments, dentinal sealants, etc. It can also be included in toothpastes, liners, bases, gels, and restorative material e.g. packing, indirect pulp capping agent, etc. Compositions in accordance with the present invention are also useful in the treatment of surfaces after periodontal surgery to decrease dentinal sensitivity and enhance tissue attachment. The compositions are active in treating various defects associated with a variety of dental and other conditions and actually chemically and physically bond to the tooth thereby remineralizing tooth structure.

As referred to herein, remineralization is the formation of hydroxyapatite. The formation of hydroxyapatite begins with exposure of a bioactive glass composition to aqueous solutions. It is believed that the sodium ions (Na+) in the bioactive glass exchanges with H+ ions in body fluids causing pH to increase. Calcium and phosphorus then migrate from the bioactive glass forming a calcium-phosphorous rich surface layer. An underlying silica rich zone slowly increases as the sodium ion in the bioactive glass continues to exchange with the hydrogen ion of the solution. After time, the calcium-phosphorous rich layer crystallizes into a hydroxyapatite material. Collagen can become structurally integrated with the apatite agglomerates. As hereinafter referred to, an effective remineralizing amount is any amount capable of forming hydroxyapatite.

As the term "a tooth structure" is used herein, it is intended to refer to any feature or features of a tooth including but not limited to enamel, dentin, pulp, tooth root structure, cementum, root dentin, coronal dentin, any dental manufacture, etc.

A bioactive glass in accordance with the present invention is a glass composition that will form a layer of hydroxycarbonate apatite in vitro when placed in a simulated body fluid. For example, the following composition by weight will provide a bioactive glass:

| | |
|---|---|
| $SiO_2$ | 40–60 |
| CaO | 10–30 |
| $Na_2O$ | 10–35 |
| $P_2O_5$ | 2–8 |
| $CaF_2$ | 0–25 |
| $B_2O_3$ | 0–10 |
| $K_2O$ | 0–8 |
| MgO | 0–5 |

Bioactive glasses with these properties provide a more efficacious material for interaction with the tooth structure. A biocompatible glass in accordance with the present invention is one that does not trigger an overwhelmingly adverse immune response.

In accordance with the present invention, it has been found that bioactive glasses of specified particle sizes are particularly useful in treating the above-mentioned conditions. Specifically, surprising results are obtained by the present invention where small and very small particles are combined. For example, when compositions including small particles that are capable of bonding with tooth structure (e.g. less than about 90 microns) as well smaller particles (e.g. less than about 10) are used in combination, the larger of these particles adhere to tooth structure and act as ionic reservoirs while the smaller are capable of entering and lodging inside of various tooth structure surface irregularities. The larger of these particles provide a reservoir of additional calcium and phosphorous so that the mineralization, or depositing of the calcium phosphate layer begun by the small particles can continue. Additional calcium and phosphorous can be leached to all tooth structure as well as to particles which have become attached to the inside or at the openings of surface irregularities of tooth structure such as dentinal tubules. This in turn provides for continuation of the entire reaction and continued growth of the smaller of these particles which have lodged inside or over the openings of such surface irregularities and can result in effectively coating or filling the surface irregularity. This excess concentration of ions of calcium and phosphorous is necessary for continued reaction of the smaller of these particles to take place because the smaller particles quickly exhaust their ions as a result of their relatively high surface area. The larger of these particles will react and release their ions more slowly as a longer term effect. Furthermore, the larger of these particles will mechanically abrade the tooth surface opening various surface irregularities allowing small particles to enter and react with the surface irregularity.

This effect is very beneficial in a variety of applications. For example, in preventing caries or decay, the composition of the present invention is capable of penetrating into the depths of the smallest of surface irregularities and receiving a continued supply of ions from larger nearby particles so that it is able to grow after exhausting its stored ion supply. This is also very useful in sealing pits and fissures and a much more effective and long lasting seal is obtained.

In some embodiments of the present invention, extremely small particles are used. For example, particles that are in the range of 2 μm to submicron fit inside dentin tubules that are approximately 1–2 μm in diameter. The occlusion of these tubules leads to a significant reduction in the amount of sensitivity after, for example, periodontal surgery. Preferably, a mixture of particles less than two microns and larger than 45 microns in diameter are used. It has been found that this combination yields a particularly effective composition.

Compositions in accordance with the present invention generally do not require time to set. Previous compositions were easily washed away by mechanical abrasion caused by brushing, exposure to mild acids in food, salivary flow or other liquids which normally come in contact with the teeth. However, some compositions in accordance with the present invention have been able to generally withstand significant agitation, rinsing with water and long term soaking in simulated saliva for five days. Moreover, many of the small particles of the present invention do not require a set time because they begin to chemically react and adhere to tooth structure as soon as they come into contact with these surfaces and fluids naturally present in the mouth. Although compositions in accordance with the present invention are effective with a single application, it is likely that multiple applications will be more efficacious.

Surprisingly, the relatively small bioactive particulate glass of the present invention does not generate a significant immune response. Moreover, it is generally not engulfed by macrophages and rendered inactive in this application.

The composition of the present invention is capable of providing a bioactive layer that will form a new structural layer which is a lasting remineralization of tooth structure. This has been verified by the reformation of a hydroxycarbonate apatite layer on dentin surfaces after treatment with compositions in accordance with the present invention with Fourier Transform Infrared spectroscopy (FTIR).

In one embodiment in accordance with the present invention, the particles have a particle size of about 20 microns with about 30 percent of the particles less than 10 microns. In another embodiment in accordance with the present invention the particles have an average particle size of 10 microns with at least 25% smaller than 2 microns.

The compositions of the present invention may be formulated into toothpaste. In fact, the particles may replace the silica currently used in toothpastes. The addition of fluoride in the glass composition will enhance and strengthen the tooth structure. In addition to direct application of the bioactive glass to the teeth, the bioactive glass composition of the present invention can also be applied in a saline or distilled water based medium.

The compositions of the present invention may also be formulated into mouthwash, gel or they may be applied by a dentist as a paste.

EXAMPLES

Figure 2:
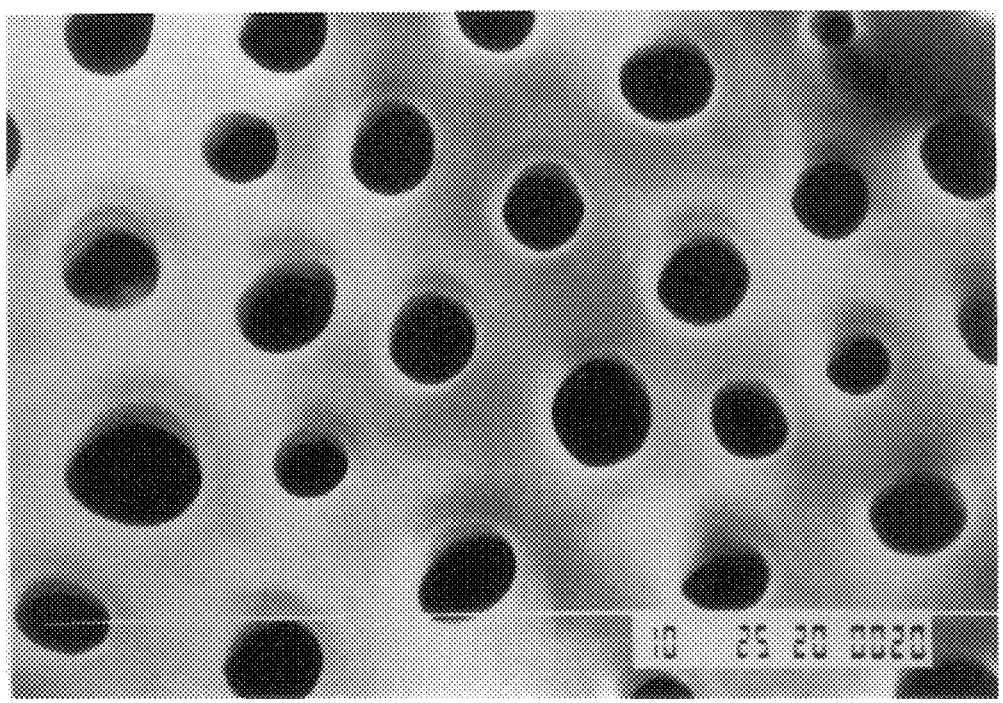
FIG. 2 is a dentin control surface that has been treated with 37% Phosphoric acid for 30 seconds to remove any smear layer after sectioning and grinding to emulate clinical sensitivity. The surface has not been treated with bioactive glass in accordance with the present invention (3000× magnification).
Figure 3:
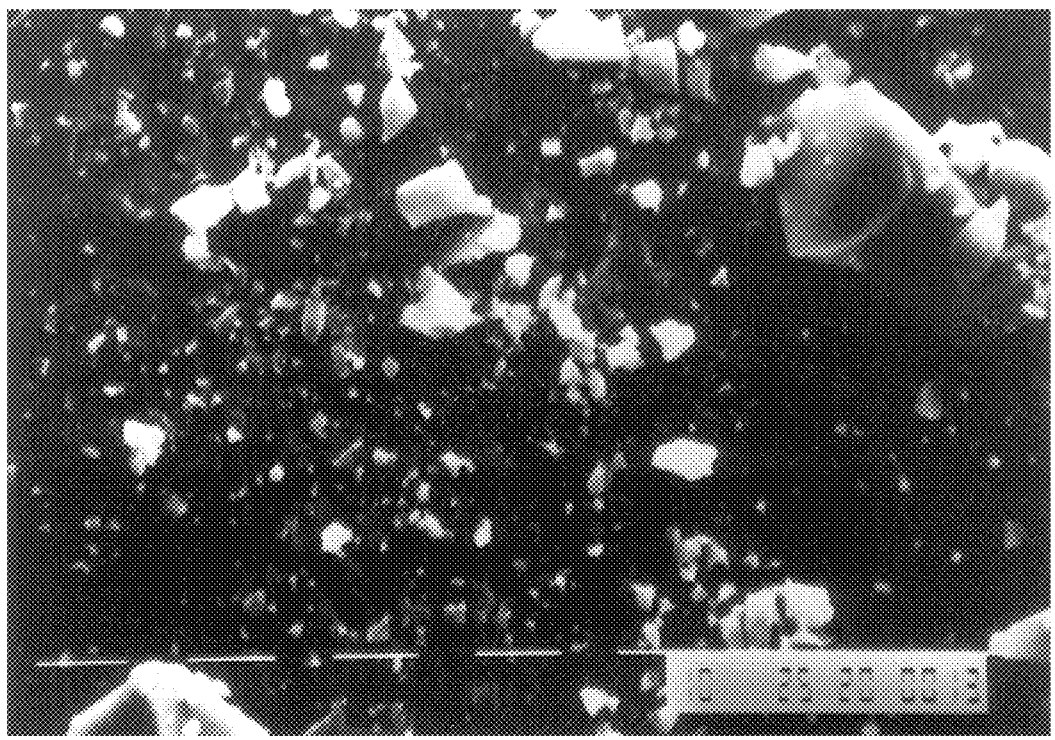
FIG. 3 is a dentin surface that has been treated with an acid etch and treated with a bioactive glass composition in accordance with the present invention in water and glycerin for 2 minutes (Particle size range submicron to 90 μm, 1000×magnification).
Figure 4:
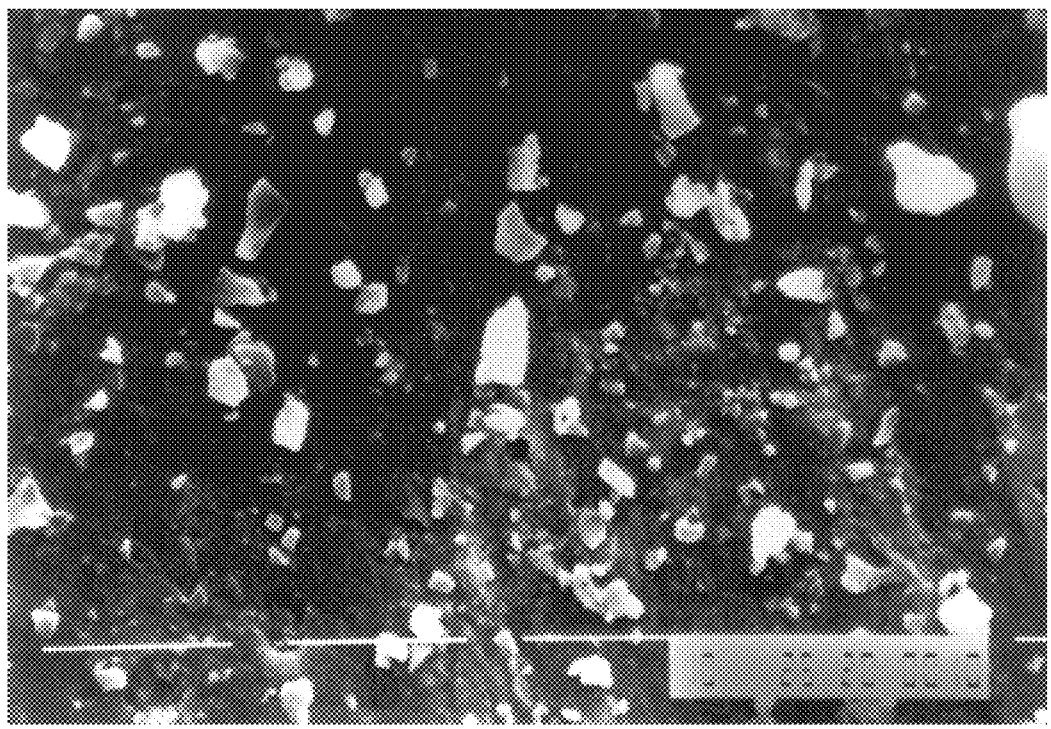
FIG. 4 is a dentin surface that has been acid etched and subsequently treated with a bioactive glass composition in accordance with the present invention in water and glycerin for 2 minutes. The surfaces were subsequently agitated and water rinsed for 2 minutes (Particle size range submicron to 20 μm, 2000×magnification).
Figure 5:
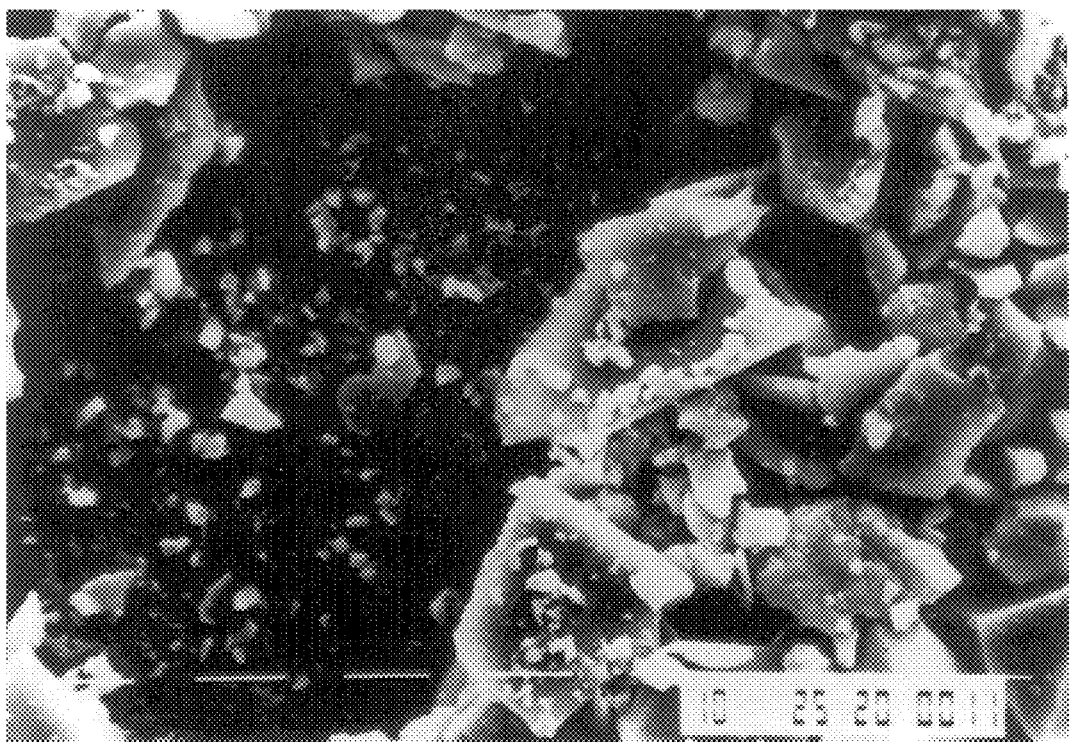
FIG. 5 is a dentin surface that has been acid etched and subsequently treated with a bioactive glass composition in accordance with the present invention and placed in water for 3 days. There was no subsequent agitation, but the surface was water rinsed for 2 minutes (Particle size range submicron to 90 μm, 2000×magnification).
Figure 6:
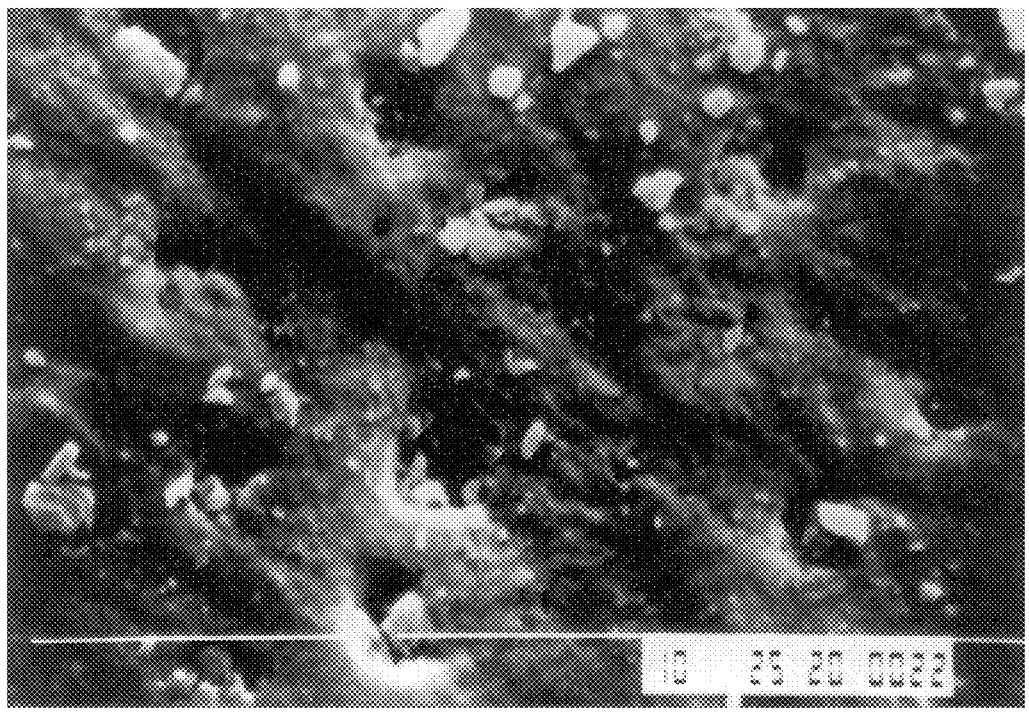
FIG. 6 is a dentin surface that has been acid etched and subsequently treated with a bioactive glass composition in accordance with the present invention in water and toothpaste for 2 minutes with agitation and a subsequent 2 minute water rinse (Particle size range submicron to 3 μm, 3000× magnification).
Figure 7:
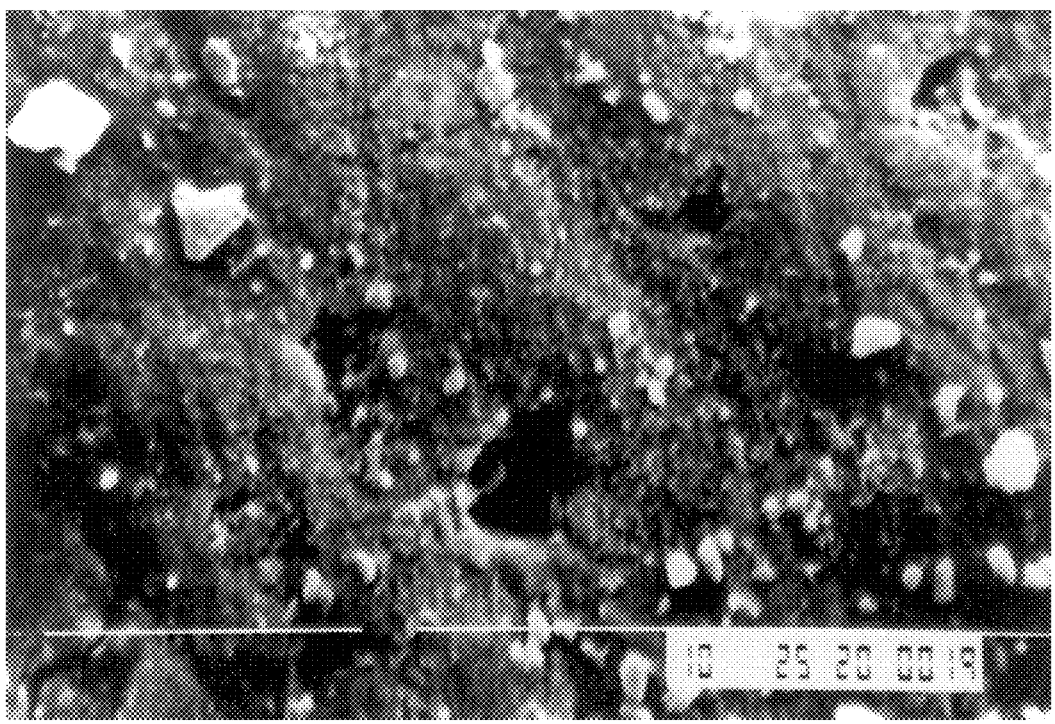
FIG. 7 is a dentin surface that has been acid etched and treated with a bioactive glass composition in accordance with the present invention in water and toothpaste for 2 minutes with agitation and water rinse for 2 minutes (Particle size range submicron to 3 μm, 3500× magnification).

The following working examples are non-limiting:

In vitro experiments were performed using a standardized slab of human tooth dentin from extracted teeth. These discs were cut from the extracted teeth using an Isomet diamond saw (Buchler Ltd.). The discs were 1.0 mm thick and the size of the tooth. The occlusal surfaces were ground on a series of wet silicon-carbide papers ranging from 320 to 600 grit. This was done to standardize the test surfaces. The surfaces were treated with 37% phosphoric acid for 60 seconds to remove the smear layer created during the grinding process and open and enlarge all the dentin tubules (See FIGS. 1 and 2). The surface was rinsed with distilled water for 20 seconds and dried with a stream of oil free air. Each slab was split in half and the experimental material placed on one-half of the specimen as described in the examples. An untreated slab with open and enlarged tubules is shown in FIGS. 1 and 2.

Scanning electron microscopy was performed on the slab surface in each group. The slabs were mounted on scanning electron microscope stubs using sliver paste. All specimens were vacuum dried, sputter coated and examined in a JEOL-T200 scanning electron microscope.

EXAMPLE 1

The starting product was a mixture containing (% by weight)

| | |
|---|---|
| $SiO_2$ | 45 |
| CaO | 24.5 |
| $Na_2O$ | 24.5 |
| $P_2O_5$ | 6 |

The mixture was melted in a covered platinum crucible at 1350° C. for 2 hours to achieve homogenization. The mixture was later quenched in deionized water at 0° C. Fritted glass was placed in an appropriate milling apparatus including ball mill, impact mill. The glass is milled for 2 hours and separated into appropriate size ranges.

The particle size range less than 90 $\mu$m was obtained using this process and confirmed by scanning electron microscopy and laser light scattering technique (Coulter LS 100). These mixtures were placed on the dentin slabs previously described.

The exposure times to the dentin varied between two minutes with scrubbing to 3 days with no agitation. The occlusion of the tubules is depicted in FIGS. 3–7. Visible in FIGS. 3–7 are total and partial occlusion of the dentin tubules with multiple size of small (1–5 $\mu$m) particles present. In addition, larger particles that are visible that will act as reservoirs for the chemical composition. Early formation of hydroxyapatite crystals is beginning on the dentin surface confirmed by FTIR.

EXAMPLE 2

Figure 8:
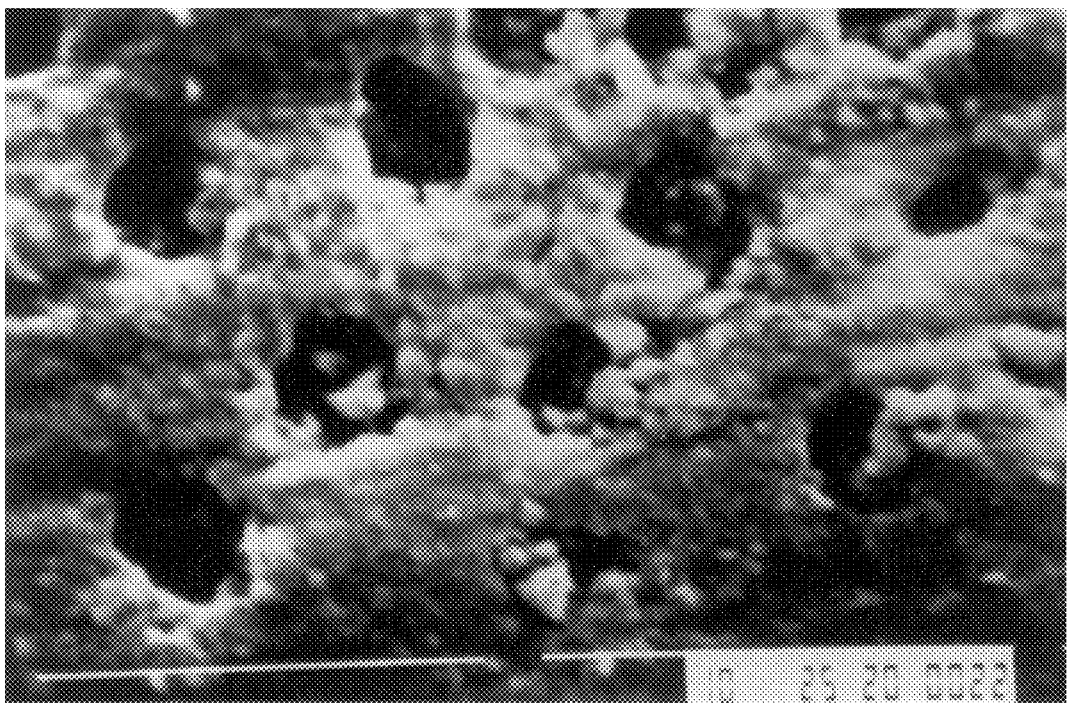
FIGS. 8 and 9 each include a dentin surface which has been acid etched with phosphoric acid, treated with a bioactive glass in accordance with the present invention for 2 minutes and immersed in a phosphate buffered saline for 5 days (Particle size range submicron).
Figure 9:
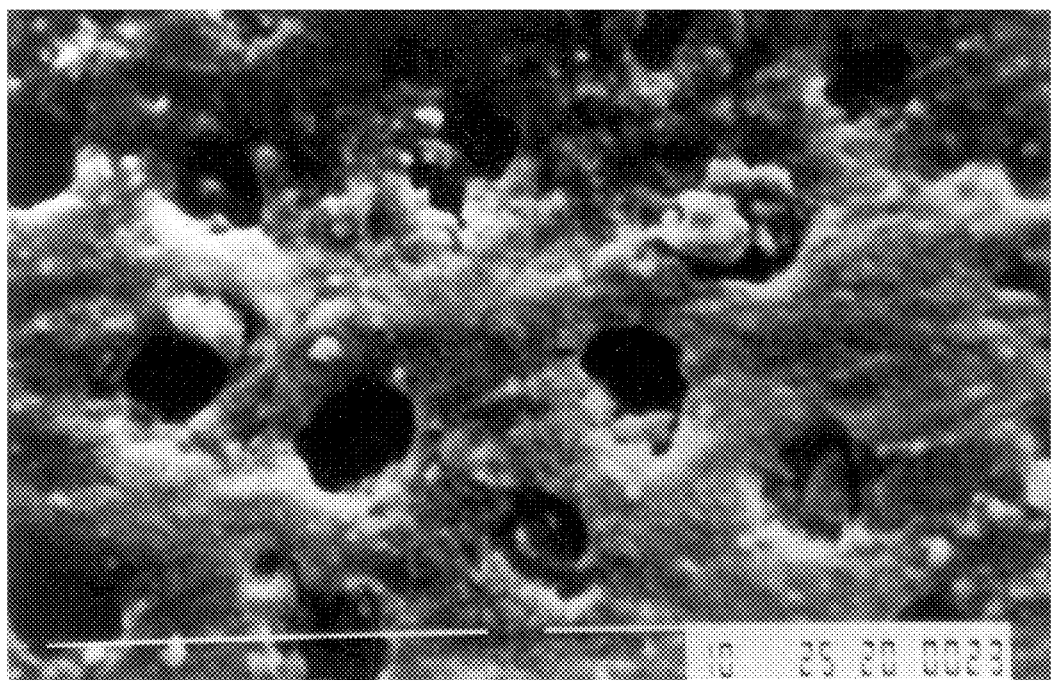

FIGS. 8 and 9 indicate the results obtainable by using submicron particles made in accordance with Example 1. The samples of FIGS. 8 and 9 are dentin surfaces which have been acid etched with phosphoric acid, treated with a bioactive glass for 2 minutes and immersed in a phosphate buffered saline for 5 days. With the lack of large particles for reservoir activity, there was less complete regeneration as confirmed by FTIR.

EXAMPLE 3

Figure 10:
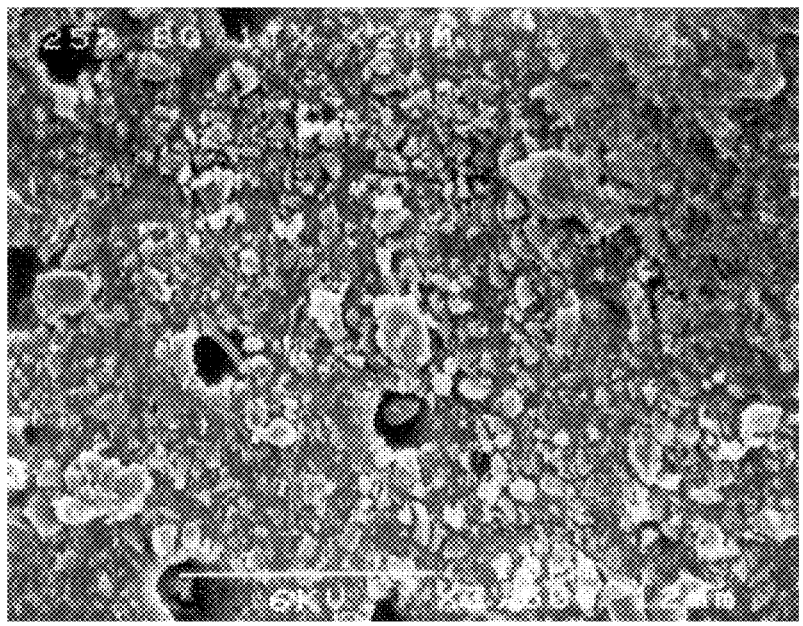
FIG. 10 depicts a dentin surface that has been acid etched and subsequently treated with a single application of a bioactive glass composition in accordance with the present invention.
Figure 11:
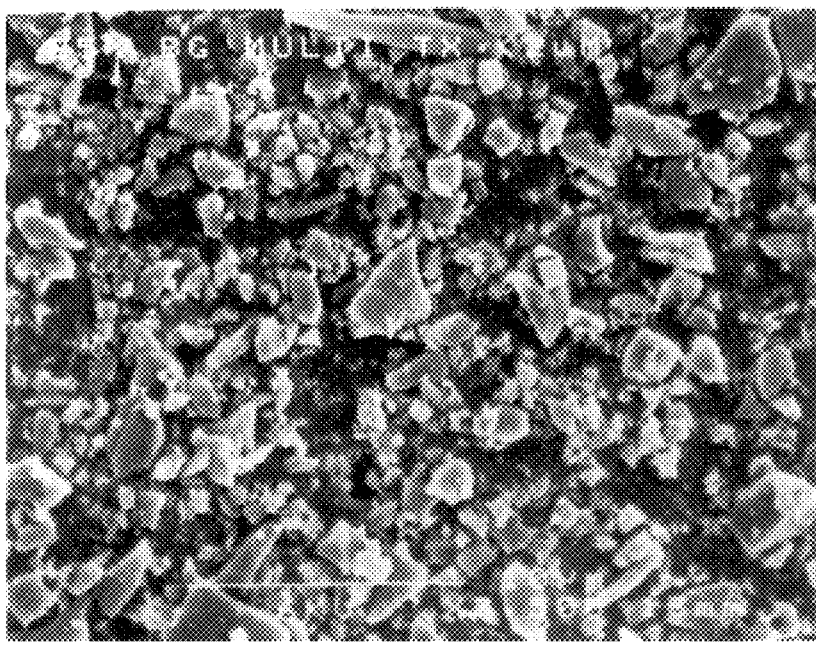
FIG. 11 depicts a dentin surface that has been acid etched and treated with three separate applications of a bioactive glass composition in accordance with the present invention.
Figure 12A:
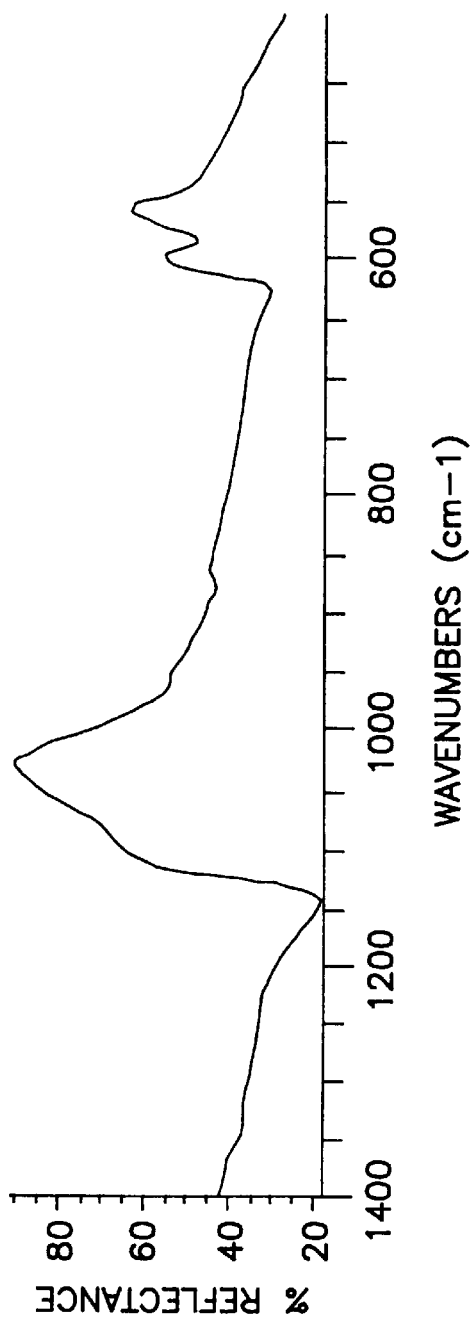
FIG. 12 is a Fourier Transform Spectroscopy (FTIR) performed on samples treated with optimal sizes and shaped particulate bioactive glass.
Figure 12B:
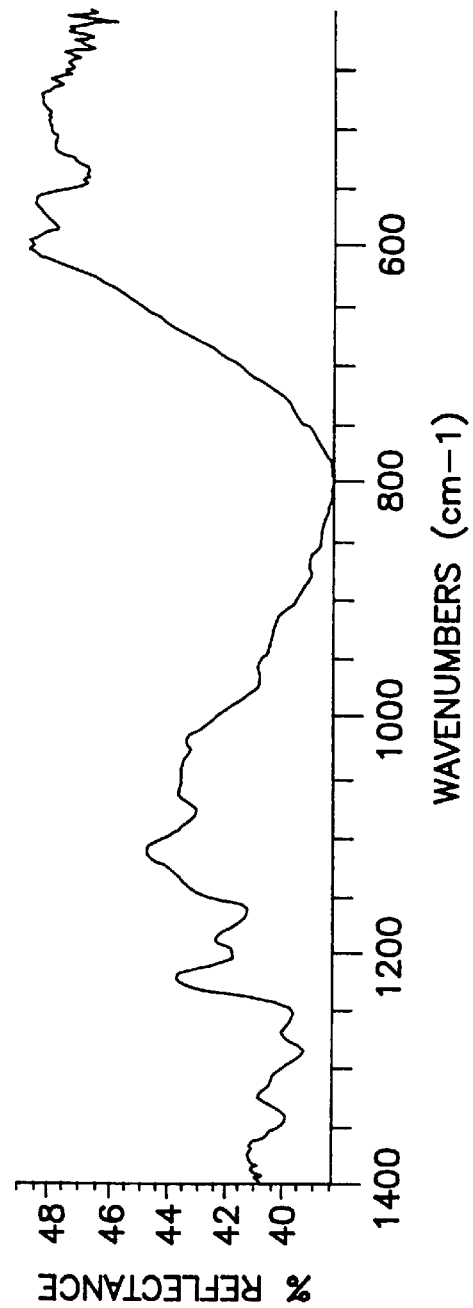
Figure 12C:
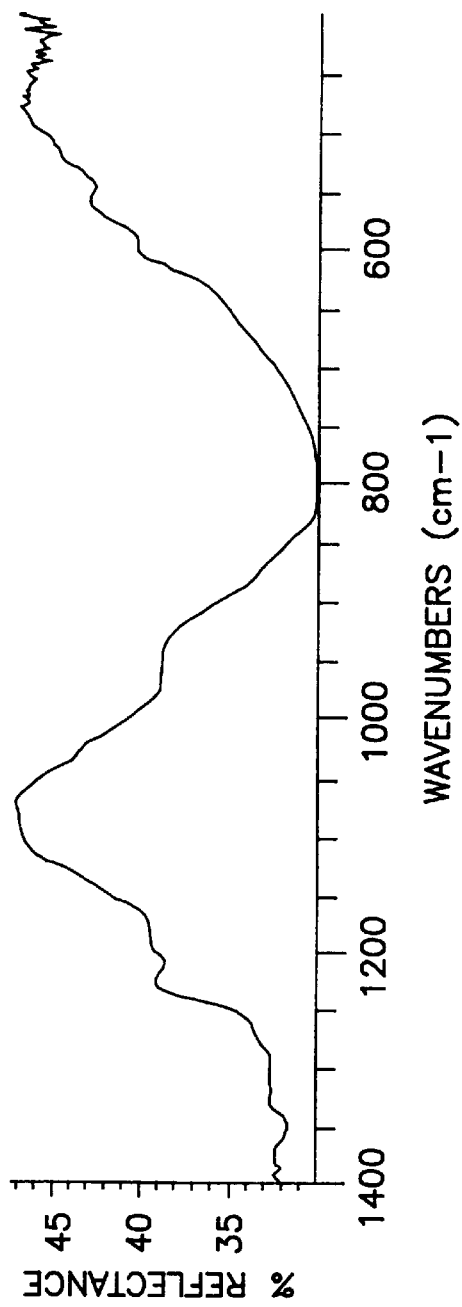
Figure 12D:
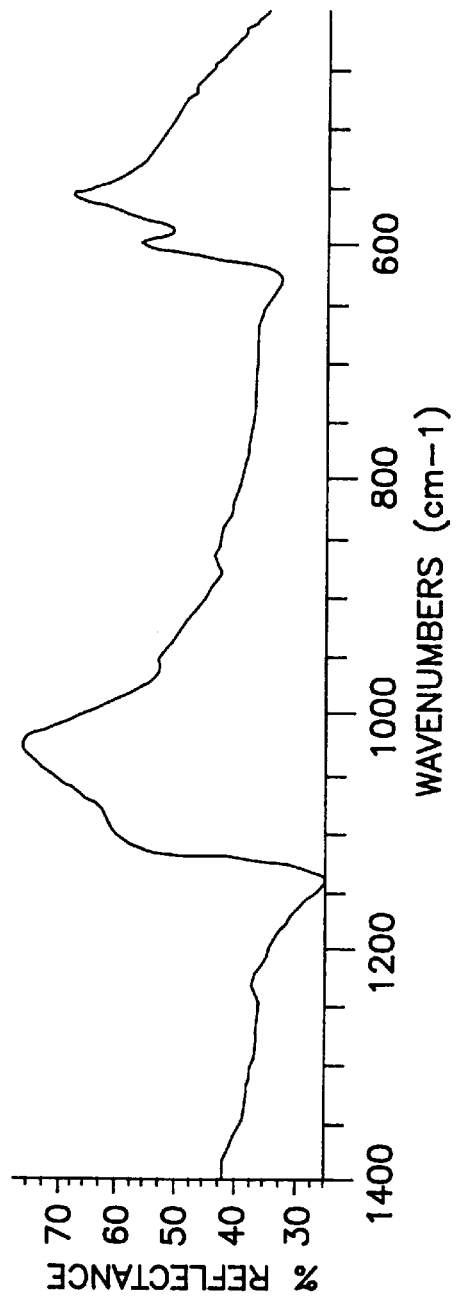

Example 3 was conducted to illustrate the benefits associated with multiple applications of compositions in accordance with the present invention. First, an acid etched dentin surface was treated with a single treatment of bioactive particulate glass for two minutes and is depicted in FIG. 10. A dentin surface which has been acid etched and treated three times for two minutes is depicted in FIG. 11.

FIG. 10 shows significant penetration and occlusion of the tubules with a bonding over the surface of the dentin. There are not many large particles visible in FIG. 10. In FIG. 11, there is even more significant penetration and occlusion of the tubules and a greater number of particles present. This demonstrates the benefits associated with multiple application including the tubules as well as increased presence of larger reservoirs of Ca and P ions. This also demonstrates interparticle welding of the larger particles to the smaller particles already bound to the surface.

EXAMPLE 4

Example 4 further illustrates the benefits associated with the use of particles less than 2 microns in combination particles greater than 45 microns in size. FTIR spectra for the following samples are included in FIG. 12 to illustrate remineralization:

Sample No. 1 Control (untreated dentin surface)

Sample No. 2 Acid etched dentin surface

Sample No. 3 Treated with particles of bioactive glass less than 2 microns in particle size for two minutes Sample No. 4 Treated with particles of bioactive glass wherein 40% were less than 2 microns, 15% were in the range of 8 to 2 microns, 15% were in the range of 8 to 20 microns, 15% were in the range of 20 to 38 microns and 15% were in the range of 38–90 microns.

As illustrated in FIG. 12, the control sample provides a representative view of the spectrum of hydroxycarbonate apatite (HCA). The shape of the peaks between wave number 1150 to 500 are very characteristic of HCA. In sample 2, the peaks are disrupted after treatment with the acid etchant, especially in the 1150 to 900 range. This indicates a loss of the mineral components of the tooth structure, Calcium and Phosphorous. Sample 3 shows a partial remineralization of the Ca and P on the tooth structure. Sample 4 was treated with the optimal size and shape mixture of bioactive glass and shows an almost complete remineralization. A photomicrograph of Sample 4 is included as FIG. 11.

EXAMPLE 5

Comparative Example 5 shows the benefits associated with the use of particles less than 10 microns in combination with particles greater than 45 microns in size over the use of just particles less than 2 microns or 53–90μ. A control sample of untreated dentin surface was used in addition to treated surfaces as described below:

| Number of Applications | Sample Composition | Score | Observations |
|---|---|---|---|
| Single | 53–90μ | 2 | About 50% occluded tubules with large particles present |
| | Control | 0 | No particles present |
| Single | <2μ | 2 | Above 50% closure, no large particles seen |
| | Control | 0 | Open tubules |
| Single | 50% 53–90μ 50% <2μ | +3 | 75% + tubules occluded |
| | Control | 0 | Open tubules |
| Multiple | 53–90μ | 2 | Partial closure of tubules with large particles present |
| | Control | 0 | Minimal occlusion seen |
| Multiple | <2μ | 2 | Partial closure of tubules with small particles present |
| | Control | 0 | Minimal occlusion seen |
| Multiple | 50% 53–90μ 50% <2μ | | Best results-- tubules closed; difficult to find open tubules |
| | Control | 0 | Minimal occlusion seen |

All samples in the above Table were subjected to a moist environment for 24 hours and then dried for 48 hours.

As seen above, the combination of particles less than 2 microns and 53–90μ provided the best results. It is believed that the presence of both size ranges permits the smaller particles which have lodged in the tubules to continue growth after they have exhausted their own Ca and P ions and are able to make use of such ions from other nearby larger particles acting as reservoirs of Ca and P ions.

Other Examples

The composition of the starting product for the following examples was the same as Example 1 except the level of $SiO_2$ was 45%, 55%, and 60%. Also, the method of preparation was different. The mixture was melted in a covered platinum crucible at 1350° C. for 2 hours to achieve homogenization. The mixture was poured into a slab, allowed to cool to room temperature and crushed with a hammer. Crushed glass fractions were then separated by sieving through a standard screen. Fractions were then separated and retained.

The particle size range less than 90 μm was obtained using this process and confirmed by scanning electron microscopy and laser light scattering technique (Coulter LS 100). These mixtures were placed on the dentin slabs previously described.

Samples containing 45%, 55%, and 60% $SiO_2$ were utilized in the preparations with the same results seen in Example 1. Again, the key to this data was the presence of the size range of particles. Present in these examples are ranges up to 60% silica with a size range in particles from submicron to 90 micron showing like reactions to Example 1 on the dentin surfaces.

Although the present invention has been described in one or more embodiments, this description is not intended to in any way limit the scope of the claims.

We claim:

1. A method for preventing tooth decay comprising contacting a tooth structure with a bioactive glass composition comprising particulate bioactive and biocompatible glass including by weight percentage:

| | |
|---|---|
| $SiO_2$ | 40–60 |
| CaO | 10–30 |
| $Na_2O$ | 10–35 |
| $P_2O_5$ | 2–8 |
| $CaF_2$ | 0–25 |
| $B_2O_3$ | 0–10 |
| $K_2O$ | 0–8 |
| MgO | 0–5, | the particulate bioactive and biocompatible glass including particles less than 90 μm and an effective remineralizing amount of particles less than about 10 μm.

2. A method for treating tooth decay comprising contacting a tooth structure with a bioactive glass composition comprising particulate bioactive and biocompatible glass including by weight percentage:

| | |
|---|---|
| $SiO_2$ | 40–60 |
| CaO | 10–30 |
| $Na_2O$ | 10–35 |
| $P_2O_5$ | 2–8 |
| $CaF_2$ | 0–25 |
| $B_2O_3$ | 0–10 |
| $K_2O$ | 0–8 |
| MgO | 0–5, | the particulate bioactive and biocompatible glass including particles less than 90 μm and an effective remineralizing amount of particles less than about 10 μm.

3. A method for preventing incipient carries comprising contacting a tooth structure with a bioactive glass composition comprising particulate bioactive and biocompatible glass including by weight percentage:

| | |
|---|---|
| $SiO_2$ | 40–60 |
| CaO | 10–30 |
| $Na_2O$ | 10–35 |
| $P_2O_5$ | 2–8 |
| $CaF_2$ | 0–25 |
| $B_2O_3$ | 0–10 |
| $K_2O$ | 0–8 |
| MgO | 0–5, | the particulate bioactive and biocompatible glass including particles less than 90 μm and an effective remineralizing amount of particles less than about 10 μm.

4. A method for remineralizing enamel comprising contacting a tooth structure with a bioactive glass composition comprising particulate bioactive and biocompatible glass including by weight percentage:

| | |
|---|---|
| $SiO_2$ | 40–60 |
| CaO | 10–30 |
| $Na_2O$ | 10–35 |
| $P_2O_5$ | 2–8 |
| $CaF_2$ | 0–25 |
| $B_2O_3$ | 0–10 |
| $K_2O$ | 0–8 |
| MgO | 0–5, | the particulate bioactive and biocompatible glass including particles less than 90 μm and an effective remineralizing amount of particles less than about 10 μm.

5. A method for incipient caries remineralization comprising contacting a tooth structure with a bioactive glass composition comprising particulate bioactive and biocompatible glass including by weight percentage:

| | |
|---|---|
| SiO$_2$ | 40–60 |
| CaO | 10–30 |
| Na$_2$O | 10–35 |
| P$_2$O$_5$ | 2–8 |
| CaF$_2$ | 0–25 |
| B$_2$O$_3$ | 0–10 |
| K$_2$O | 0–8 |
| MgO | 0–5, | the particulate bioactive and biocompatible glass including particles less than 90 μm and an effective remineralizing amount of particles less than about 10 μm.

6. A method for sealing fissures in tooth structure comprising contacting a tooth structure with a bioactive glass composition comprising particulate bioactive and biocompatible glass including by weight percentage:

| | |
|---|---|
| SiO$_2$ | 40–60 |
| CaO | 10–30 |
| Na$_2$O | 10–35 |
| P$_2$O$_5$ | 2–8 |
| CaF$_2$ | 0–25 |
| B$_2$O$_3$ | 0–10 |
| K$_2$O | 0–8 |
| MgO | 0–5, | the particulate bioactive and biocompatible glass including particles less than 90 μm and an effective remineralizing amount of particles less than about 10 μm.

7. A method for sealing pits in tooth structure comprising contacting a tooth structure with a bioactive glass composition comprising particulate bioactive and biocompatible glass including by weight percentage:

| | |
|---|---|
| SiO$_2$ | 40–60 |
| CaO | 10–30 |
| Na$_2$O | 10–35 |
| P$_2$O$_5$ | 2–8 |
| CaF$_2$ | 0–25 |
| B$_2$O$_3$ | 0–10 |
| K$_2$O | 0–8 |
| MgO | 0–5, | the particulate bioactive and biocompatible glass including particles less than 90 μm and an effective remineralizig amount of particles less than about 10 μm.

8. A method for lining tooth structure comprising contacting a tooth structure with a bioactive glass composition comprising particulate bioactive and biocompatible glass including by weight percentage:

| | |
|---|---|
| SiO$_2$ | 40–60 |
| CaO | 10–30 |
| Na$_2$O | 10–35 |
| P$_2$O$_5$ | 2–8 |
| CaF$_2$ | 0–25 |
| B$_2$O$_3$ | 0–10 |
| K$_2$O | 0–8 |
| MgO | 0–5, | the particulate bioactive and biocompatible glass including particles less than 90 μm and an effective remineralizing amount of particles less than about 10 μm.

9. A method for capping pulp comprising contacting a tooth structure with a bioactive glass composition comprising particulate bioactive and biocompatible glass including by weight percentage:

| | |
|---|---|
| SiO$_2$ | 40–60 |
| CaO | 10–30 |
| Na$_2$O | 10–35 |
| P$_2$O$_5$ | 2–8 |
| CaF$_2$ | 0–25 |
| B$_2$O$_3$ | 0–10 |
| K$_2$O | 0–8 |
| MgO | 0–5, | the particulate bioactive and biocompatible glass including particles less than 90 μm and an effective remineralizing amount of particles less than about 10 μm.

10. A method for treating tooth hypersensitivity comprising contacting a tooth structure with a bioactive glass composition comprising particulate bioactive and biocompatible glass including by weight percentage:

| | |
|---|---|
| SiO$_2$ | 40–60 |
| CaO | 10–30 |
| Na$_2$O | 10–35 |
| P$_2$O$_5$ | 2–8 |
| CaF$_2$ | 0–25 |
| B$_2$O$_3$ | 0–10 |
| K$_2$O | 0–8 |
| MgO | 0–5, | the particulate bioactive and biocompatible glass including particles less than 90 μm and an effective remineralizing amount of particles less than about 10 μm.

11. A method for treating tooth structure after periodontal surgery comprising contacting a tooth structure with a bioactive glass composition comprising particulate bioactive and biocompatible glass including by weight percentage:

| | |
|---|---|
| SiO$_2$ | 40–60 |
| CaO | 10–30 |
| Na$_2$O | 10–35 |
| P$_2$O$_5$ | 2–8 |
| CaF$_2$ | 0–25 |
| B$_2$O$_3$ | 0–10 |
| K$_2$O | 0–8 |
| MgO | 0–5, | the particulate bioactive and biocompatible glass including particles less than 90 μm and an effective remineralizing amount of particles less than about 10 μm.

12. A method for preventing tooth decay comprising contacting a tooth structure with a bioactive glass composition comprising particulate bioactive and biocompatible glass including by weight percentage:

| | |
|---|---|
| SiO$_2$ | 40–60 |
| CaO | 10–30 |
| Na$_2$O | 10–35 |
| P$_2$O$_5$ | 2–8 |
| CaF$_2$ | 0–25 |
| B$_2$O$_3$ | 0–10 |

-continued

| | |
|---|---|
| K$_2$O | 0–8 |
| MgO | 0–5, | the particulate bioactive and biocompatible glass including particles between 45µ and 90 µm and an effective remineralizing amount of particles less than about 10 µm.

13. A method for treating tooth decay comprising contacting a tooth structure with a bioactive glass composition comprising particulate bioactive and biocompatible glass including by weight percentage:

| | |
|---|---|
| SiO$_2$ | 40–60 |
| CaO | 10–30 |
| Na$_2$O | 10–35 |
| P$_2$O$_5$ | 2–8 |
| CaF$_2$ | 0–25 |
| B$_2$O$_3$ | 0–10 |
| K$_2$O | 0–8 |
| MgO | 0–5, | the particulate bioactive and biocompatible glass including particles between 45µ and 90 µm and an effective remineralizing amount of particles less than about 10 µm.

14. A method for preventing incipient carries comprising contacting a tooth structure with a bioactive glass composition comprising particulate bioactive and biocompatible glass including by weight percentage:

| | |
|---|---|
| SiO$_2$ | 40–60 |
| CaO | 10–30 |
| Na$_2$O | 10–35 |
| P$_2$O$_5$ | 2–8 |
| CaF$_2$ | 0–25 |
| B$_2$O$_3$ | 0–10 |
| K$_2$O | 0–8 |
| MgO | 0–5, | the particulate bioactive and biocompatible glass including particles between 45µ and 90 µm and an effective remineralizing amount of particles less than about 10 µm.

15. A method for remineralizing enamel comprising contacting a tooth structure with a bioactive glass composition comprising particulate bioactive and biocompatible glass including by weight percentage:

| | |
|---|---|
| SiO$_2$ | 40–60 |
| CaO | 10–30 |
| Na$_2$O | 10–35 |
| P$_2$O$_5$ | 2–8 |
| CaF$_2$ | 0–25 |
| B$_2$O$_3$ | 0–10 |
| K$_2$O | 0–8 |
| MgO | 0–5, | the particulate bioactive and biocompatible glass including particles between 45µ and 90 µm and an effective remineralizing amount of particles less than about 10 µm.

16. A method for incipient caries remineralization comprising contacting a tooth structure with a bioactive glass composition comprising particulate bioactive and biocompatible glass including by weight percentage:

| | |
|---|---|
| SiO$_2$ | 40–60 |
| CaO | 10–30 |
| Na$_2$O | 10–35 |
| P$_2$O$_5$ | 2–8 |
| CaF$_2$ | 0–25 |
| B$_2$O$_3$ | 0–10 |
| K$_2$O | 0–8 |
| MgO | 0–5, | the particulate bioactive and biocompatible glass including particles between 45µ and 90 µm and an effective remineralizing amount of particles less than about 10 µm.

17. A method for sealing fissures in tooth structure comprising contacting a tooth structure with a bioactive glass composition comprising particulate bioactive and biocompatible glass including by weight percentage:

| | |
|---|---|
| SiO$_2$ | 40–60 |
| CaO | 10–30 |
| Na$_2$O | 10–35 |
| P$_2$O$_5$ | 2–8 |
| CaF$_2$ | 0–25 |
| B$_2$O$_3$ | 0–10 |
| K$_2$O | 0–8 |
| MgO | 0–5, | the particulate bioactive and biocompatible glass including particles between 45 µ and 90 µm and an effective remineralizing amount of particles less than about 10 µm.

18. A method for sealing pits in tooth structure comprising contacting a tooth structure with a bioactive glass composition comprising particulate bioactive and biocompatible glass including by weight percentage:

| | |
|---|---|
| SiO$_2$ | 40–60 |
| CaO | 10–30 |
| Na$_2$O | 10–35 |
| P$_2$O$_5$ | 2–8 |
| CaF$_2$ | 0–25 |
| B$_2$O$_3$ | 0–10 |
| K$_2$O | 0–8 |
| MgO | 0–5, | the particulate bioactive and biocompatible glass including particles between 45µ and 90 µm and an effective remineralizing amount of particles less than about 10 µm.

19. A method for lining tooth structure comprising contacting a tooth structure with a bioactive glass composition comprising particulate bioactive and biocompatible glass including by weight percentage:

| | |
|---|---|
| SiO$_2$ | 40–60 |
| CaO | 10–30 |
| Na$_2$O | 10–35 |
| P$_2$O$_5$ | 2–8 |
| CaF$_2$ | 0–25 |
| B$_2$O$_3$ | 0–10 |
| K$_2$O | 0–8 |
| MgO | 0–5, | the particulate bioactive and biocompatible glass including particles between 45µ and 90 µm and an effective remineralizing amount of particles less than about 10 µm.

20. A method for capping pulp comprising contacting a tooth structure with a bioactive glass composition comprising particulate bioactive and biocompatible glass including by weight percentage:

| | |
|---|---|
| SiO$_2$ | 40–60 |
| CaO | 10–30 |
| Na$_2$O | 10–35 |
| P$_2$O$_5$ | 2–8 |
| CaF$_2$ | 0–25 |
| B$_2$O$_3$ | 0–10 |
| K$_2$O | 0–8 |
| MgO | 0–5, | the particulate bioactive and biocompatible glass including particles between 45μ and 90 μm and an effective remineralizing amount of particles less than about 10 μm.

21. A method for treating tooth hypersensitivity comprising contacting a tooth structure with a bioactive glass composition comprising particulate bioactive and biocompatible glass including by weight percentage:

| | |
|---|---|
| SiO$_2$ | 40–60 |
| CaO | 10–30 |
| Na$_2$O | 10–35 |
| P$_2$O$_5$ | 2–8 |
| CaF$_2$ | 0–25 |
| B$_2$O$_3$ | 0–10 |
| K$_2$O | 0–8 |
| MgO | 0–5, | the particulate bioactive and biocompatible glass including particles between 45μ and 90 μm and an effective remineralizing amount of particles less than about 10 μm.

22. A method for treating tooth structure after periodontal surgery comprising contacting a tooth structure with a bioactive glass composition comprising particulate bioactive and biocompatible glass including by weight percentage:

| | |
|---|---|
| SiO$_2$ | 40–60 |
| CaO | 10–30 |
| Na$_2$O | 10–35 |
| P$_2$O$_5$ | 2–8 |
| CaF$_2$ | 0–25 |
| B$_2$O$_3$ | 0–10 |
| K$_2$O | 0–8 |
| MgO | 0–5, | the particulate bioactive and biocompatible glass including particles between 45μ and 90 μm and an effective remineralizing amount of particles less than about 10 μm.

* * * * *